US00PP17482P3

(12) United States Plant Patent
Davidson

(10) Patent No.: US PP17,482 P3
(45) Date of Patent: Mar. 6, 2007

(54) HYBRID TEA ROSE PLANT NAMED 'HADQUE'

(50) Latin Name: *Rosa hybrida*
Varietal Denomination: HADQUE

(76) Inventor: Harvey Daniel Davidson, 3 El Verano Rd., Orinda, CA (US) 94563

( * ) Notice: Subject to any disclaimer, the term of this patent is extended or adjusted under 35 U.S.C. 154(b) by 54 days.

(21) Appl. No.: 11/159,680

(22) Filed: Jun. 23, 2005

(65) Prior Publication Data

US 2006/0294629 P1 Dec. 28, 2006

(51) Int. Cl.
*A01H 5/00* (2006.01)

(52) U.S. Cl. ..... Plt./130

(58) Field of Classification Search ..... Plt./130, Plt./132, 134, 137
See application file for complete search history.

*Primary Examiner*—Howard J. Locker

(57) ABSTRACT

A new and distinct hybrid tea rose cultivar named 'Hadque', particularly characterized by having stems without prickles; large yellow flowers which are lightly pink shaded; flowers borne singly and having strong fragrance; rapid repeat bloom, and the plant being bushy and upright.

1 Drawing Sheet

Botanical/commercial classification: *Rosa hybrida*/Hybrid Tea Rose Plant.

BACKGROUND AND SUMMARY OF THE INVENTION

The present invention relates to a new and distinctive cultivar of rose plant of the Hybrid Tea class, which was originated by my crossing 'KIKA' as the seed parent with 'REMEMBER ME' as the pollen parent.

Among the novel characteristics possessed by the new cultivar which distinguish it from:

(a) All other cultivars of which I am aware are:
(1) Prickles being absent from any stems.
(2) Large yellow flower with light pink shading.
(3) Single flower to the stem.
(3) Strong fragrance.
(4) Very consistent free bloomer.

(b) Seed parent: White hybrid tea; typically in clusters of three flowers; no prickles.

Pollen parent: Copper, red-orange, yellow hybrid tea; has prickles. Asexual reproduction of the new rose cultivar by budding onto the rootstock 'Dr. Huey', as performed at Vasco, Calif., shows that the aforementioned and all other distinctive characteristics come true to form and are established and transmitted through succeeding propagations. The cultivar name of this plant is 'Hadque'. The plant is being marketed under the commercial name of 'Smooth Queen'.

BRIEF DESCRIPTION OF THE DRAWING/ PHOTOGRAPH

The accompanying photographic illustration/drawing shows typical specimens of the vegetative growth and flowers of the new cultivar in different stages of development and as depicted in color as nearly true as it is reasonably possible to make the same in a color illustration of this character.

DETAILED BOTANICAL DESCRIPTION

The following is a detailed description of my new cultivar, with color terminology in accordance with The Royal Horticultural Society Colour Chart (R.H.S.C.C.) The terminology used in the color description herein refers to plate numbers such as: 'Yellow Group 16A' found in Fan 1 of The Royal Horticultural Society Colour Chart.

Parentage:
*Seed parent.*—IRAR registered: 'KIKA'; Class: Hybrid Tea; Not patented.
*Pollen parent.*—'REMEMBER ME'; Class — Hybrid Tea; Not patented.

The following observations are made of specimens grown outdoors in Orinda, Contra Costa County, Calif., in the month of October, 2003.

FLOWER

Blooming habit:
A. Bud:
(*1*) *Size.*—Sepals enclosed, 22–24 mm from base of sepals to top of bud.
(*2*) *Form.*—Ovoid.
(*3*) *Sepals.*—Fully mature 40 to 45 mm in length; 8 to 10 mm extension beyond bud; no serration shown on sepal edges. Generally 3 out of 5 sepals show appendages on each side, 5 to 8 mm length. Sepals show glandular development on edges. Heavy cotton matting on inner surface, fine matting on outer surface. Outside color: Yellow Green Group 146C and B; inside: Yellow Green Group 146C with shadings of Greyed Red Group 181C.
(*4*) *Peduncles.*—Length — 6 to 7 cm. Surface: smooth. some fine hairs, no glandular hairs, no prickles. Strength: firm. Color: near to Yellow Green 146C with shades of Greyed Orange Group 178D.
(*5*) *Receptacle.*—Shape: oblong, 10–12 mm diameter; Color: same as peduncle.

(6) *Color.*—When sepals first divide, outside bud petals: Yellow Orange 23C with shadings near to Red Group 47B, 47C, and 47D.

B. Bloom:

(1) *Size.*—When open: 11–12 cm.

(2) *Borne.*—One flower per stem.

(3) *Form.*—Globular.

(4) *Petalage.*—Average — 34 to 36.

(5) *Color.*—Early open: (upper and lower surfaces) outside petals with mixed shadings of Red Group 55C and 55D; inside petals near Yellow Orange 22C and 22D. Aging petals: (upper and lower surfaces) near Red Group 36C and D with inner shading of Yellow Orange Group 20C and 20D.

C. Petals:

(1) *Texture.*—Firm.

(2) *Appearance.*—Flexed.

(3) *Form.*—Early stages symmetrically spaced.

(4) *Arrangement.*—Regular.

(5) *Petaloids in center.*—Average 4 to 6.

(6) *Persistance.*—Petals hold well; drop cleanly at end of bloom.

(7) *Fragrance.*—Strong.

(8) *Lasting quality.*—On bush 8–9 days; as cut flowers 5–6 days.

REPRODUCTIVE ORGANS

A. Stamen:

(1) *Arrangement.*—Regular around styles.

(2) *Number.*—Average: 165–175.

(3) *Length.*—Average: 10 to 12 mm from base.

(4) *Filaments.*—Color: Close to Yellow Orange Group 16A.

(5) *Anthers.*—Color: Close to Yellow Orange Group 16A.

(6) *Pollen.*—Color: Close to Yellow Orange Group 16A.

B. Pistil:

(1) *Styles.*—Length: 8–12 mm from center of ovary; number 146–156; color: near to White Group 155A; sparsely coated with white hairs.

(2) *Stigma.*—Color: Close to Yellow Group 13A.

(3) *Ovary.*—Shape: Oblong 7–8 mm center cross section at sepal base.

C. Hips: Does not set seed.

PLANT

A. Form: Upright.

B. Growth: Height: average 1: Width: average 50 cm.

C. Stem length: Basal break to flower bud tip: average 90–100 cm.

D. Foliage: Compound of 3 to 5 leaflets on bloom stem: 5 to 7 leaflets on main canes.

(1) *Quality.*—Stems well covered.

(2) *Color.*—New foliage: Upper side near Greyed Purple 183B: under side near to Greyed Purple 184A. Old foliage: Upper side near to Yellow Green 146A; under side near to Yellow Green 146B.

(3) *Shape.*—Mature 5 leaflet: Length: stipule base to tip of leaflet — 12–13 cm. Center end leaflet: Oval and pointed. Length: 5–6 cm: Width: 4–4½ cm.

(4) *Texture.*—Firm, leathery, semi-glossy.

(5) *Edge.*—Serration on outer edge: Average 5 to 6 points per 1 cm, with ½ to 1 mm peak.

(6) *Rachis.*—Very few glandular hairs on lower and upper side. 3 to 4 prickles on lower side, length; 1–2 mm, form; straight.

(7) *Stipules.*—Length 14 to 15 mm; auricle to 3–4 mm. Edge of stipule to tip of auricle with many glandular hairs.

E. Resistance to disease: Powdery mildew, rust and blackspot: good.

F. Wood:

(1) *New wood.*—Color close to Yellow Green 146C; shadings near to Greyed Orange Group 178D; Bark — smooth.

(2) *Old wood.*—Color close to Yellow Green Group 146B; Bark smooth.

G. Prickles: None.

H. Winter hardiness: Average.

I claim:

1. A new and distinct cultivar of hybrid tea rose plant substantially as herein shown and described, and characterized in particular by its large yellow and slightly pink shaded flowers which are borne singly and bear strong fragrance, its consistent free blooming habit, the absence of prickles on any stems, with the plant being bushy and upright, of medium height, and exhibiting good resistance to powdery mildew, rust, and blackspot.

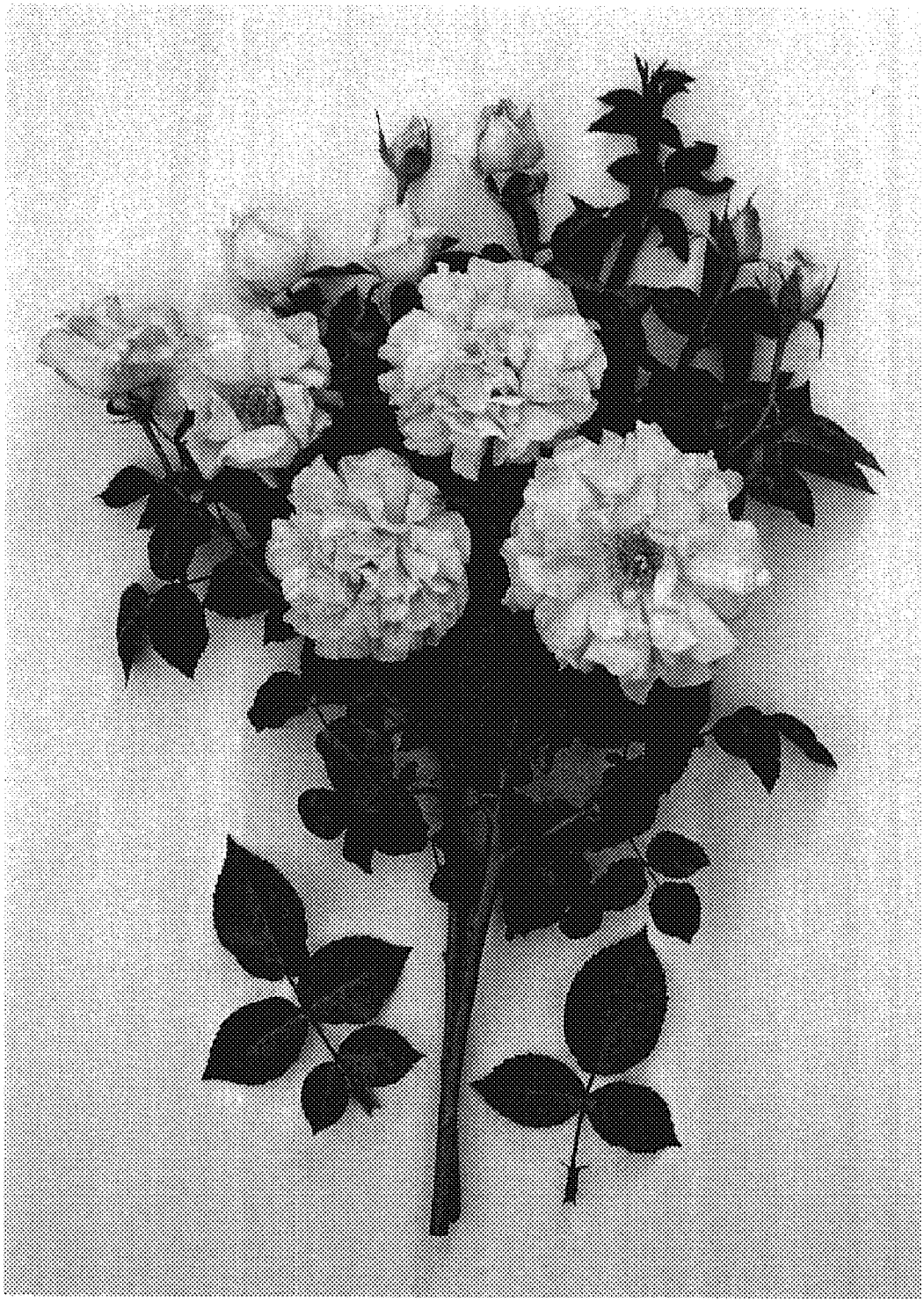

* * * * *